United States Patent [19]

Tantau

[11] Patent Number: Plant 5,707

[45] Date of Patent: Apr. 1, 1986

[54] ROSE PLANT TANATESIL

[75] Inventor: Mathias Tantau, Uetersen, Fed. Rep. of Germany

[73] Assignee: Jackson & Perkins Company, Medford, Oreg.

[21] Appl. No.: 634,793

[22] Filed: Jul. 26, 1984

[51] Int. Cl.[4] ..... A01H 5/00

[52] U.S. Cl. ..... Plt./26

[58] Field of Search ..... Plt./26

*Primary Examiner*—Robert E. Bagwill

*Attorney, Agent, or Firm*—Klarquist, Sparkman, Campbell, Leigh & Whinston

[57] ABSTRACT

A floribunda rose variety having a vigorous plant, large foliage, pink blooms having approximately 45 petals, slight fragrance, absence of prickles, long vase life, and good resistance to rose powdery mildew.

1 Drawing Figure

This present invention relates to a new and distinct variety of rose plant of the floribunda class which was originated by me by crossing an unnamed variety with an unnamed variety.

The primary objective of this breeding was to produce a new rose variety especially suitable for use as a producer of cut flowers having no thorns, very long vase life, and attractive color. This objective was substantially achieved, along with other desirable improvements, as evidenced by the following unique combination of characteristics which are outstanding in the new variety and which distinguish it from its parents, as well as from all other varieties of which I am aware:

1. A vigorous plant.
2. Large, dark green foliage.
3. Good resistance to rose powdery mildew.
4. Rose pink blooms of approximately 45 petals.
5. Very slight fragrance.
6. Exceptionally long vase life — 10 to 14 days commonly.
7. Absence of prickles.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—An unnamed variety.

*Pollen plant.*—An unnamed variety.

Classification:

*Botanical.*—Rosa hybrid.

*Commercial.*—Floribunda.

FLOWER

Observations made from specimens grown in a greenhouse at Irvine, Calif. in December.

Blooming habit: Continuous.

Bud:

*Size.*—$1\frac{1}{4}''$ when petals start to unfurl.

*Form.*—Pointed ovoid.

*Color.*—When sepals first divide, Red 52B. When half blown, upper side of petals Red 52B; lower side of petals Red 52C.

*Sepals.*—Color: Green 138A. Surface texture: Without pubescence or glands. Three appendaged sepals lightly appendaged. Two unappendaged sepals hairy edged.

*Receptacle.*—Color: Green 138A. Shape: Funnel. Size: Large, long. Surface: Smooth.

*Peduncle.*—Length: Short. Surface: Nearly smooth with some very fine hairs, occasional glands. Color: Light green. Strength: Stiff, erect.

*Opening.*—Very slowly, spiral, rarely opens completely.

Bloom:

*Size.*—Medium. Average open size: $3\frac{1}{2}''$.

Borne.—Singly, in clusters — irregular.

*Stems.*—Long, strong.

*Form.*—When first open, high centered to globular. Permanence: Retains its form to the end.

*Petalage.*—Number of petals under normal conditions: 45.

*Color.*—Center of flower: Upper side of petals Red 52B; reverse side of petals Red 52C; base of petals have a small area at point of attachment that is pale yellow. Major color: Commonly called rose pink; equivalent to R.H.S. Red Group 52B.

*Variegations.*—Occasional vegetative streak on outer petals.

*Discoloration.*—General tonality at end of first day: No change. Third day: Lightens to Red Group 52C.

*Fragrance.*—Slight.

Petals:

*Texture.*—Thin.

*Shape.*—Round.

*Form.*—Tips slightly recurved.

*Arrangement.*—Imbricated, sometimes quartered. Petaloids in center: few, small.

*Persistence.*—Hang on and dry.

*Lastingness.*—On the plant, very long. As cut flower, very long.

Reproductive parts:

*Anthers.*—Medium. Color: Yellow. Arrangement: Regular around styles.
*Filaments.*—Color: Greenish white.
*Styles.*—Color: Greenish white.
*Stigmas.*—Color: Greenish white.

PLANT

Form: Bush.
Growth: Very vigorous.
Foliage: Number of leaflets on normal mid-stem leaves: 5, sometimes 7.
*Size.*—Large.
*Quantity.*—Normal.
*Color.*—New foliage: Greyed Purple 183A. Old foliage: Dark green, close to Green 133A.
Leaflets:
*Shape.*—Broadly oval.
*Texture.*—Leathery on upper side.
*Edge.*—Serrated.
*Serration.*—Single, large.
*Petiole.*—Rachis: Color: Reddish. Underside: Smooth.

*Stipules.*—Long, bearded.
*Disease resistance.*—Resistant to mildew under normal growing conditions at Irvine, Calif.
Wood:
*New wood.*—Color: Light green. Bark: Smooth.
*Old wood.*—Color: Green. Bark: Smooth.
Prickles:
*Quantity.*—On main canes from base: None. On laterals from main canes: None.
Small prickles:
*Quantity.*—On main stalks: None. On laterals: None.

I claim:

1. A new and distinct variety of rose plant of the floribunda class, substantially as herein shown and described, characterized particularly as to novelty by the unique combination of vigorous greenhouse growth, stems without prickles, rose pink buds and blooms, exceptional vase life, slight fragrance and resistance to rose powdery mildew.

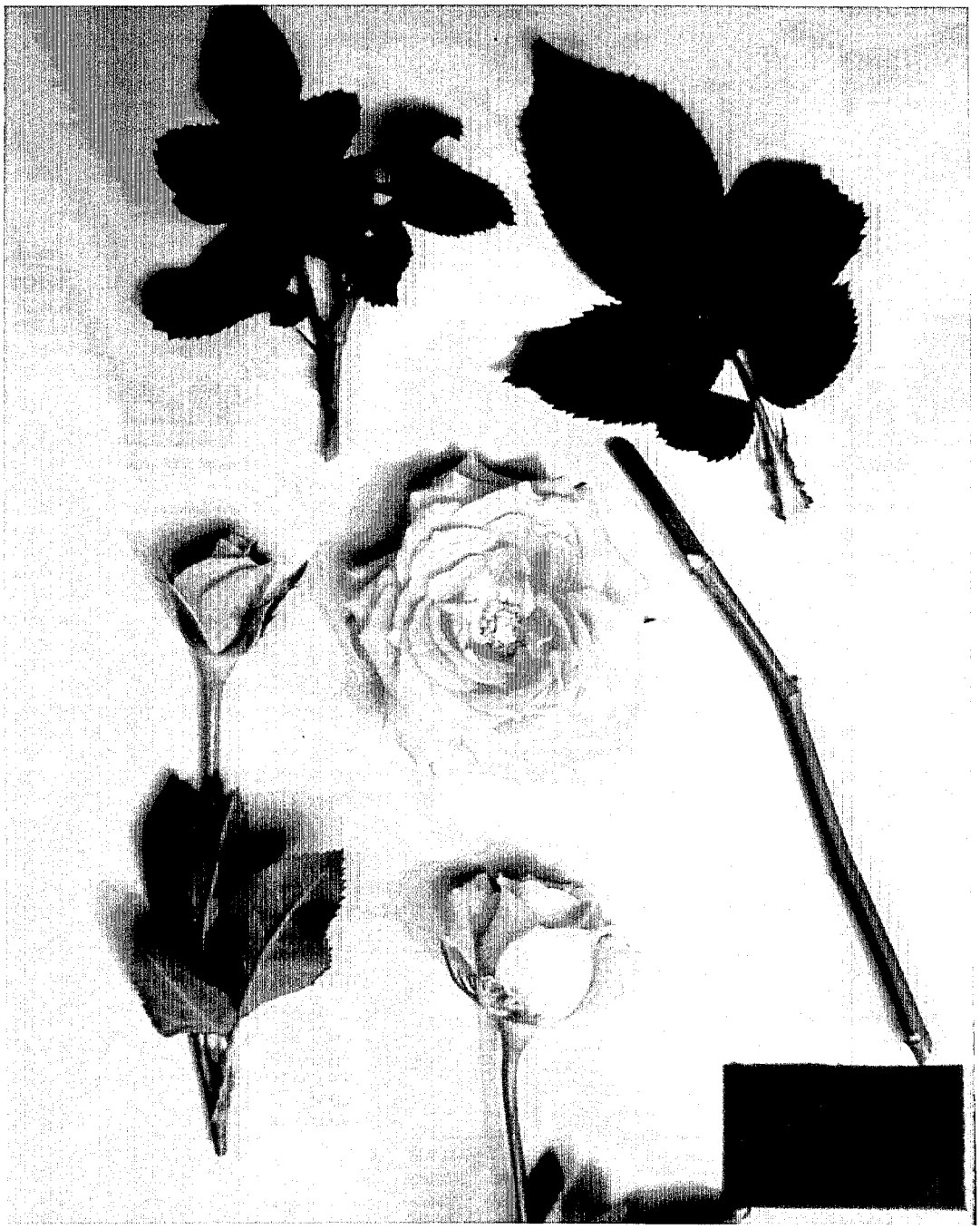

* * * * *